US012773385B2

(12) United States Patent
Kerr et al.

(10) Patent No.: US 12,773,385 B2
(45) Date of Patent: Oct. 27, 2026

(54) MESO-ABRASIVE DENTIFRICE AND SYSTEM FOR USING SAME

(71) Applicant: Premier Dental Products Company, LLC, Plymouth Meeting, PA (US)

(72) Inventors: Sean H. Kerr, Wallingford, PA (US); Victoriya Shtessel-Nemzer, Newtown, PA (US)

(73) Assignee: Premier Dental Products Company, LLC, Plymouth Meeting, PA (US)

( * ) Notice: Subject to any disclaimer, the term of this patent is extended or adjusted under 35 U.S.C. 154(b) by 766 days.

(21) Appl. No.: 17/732,147

(22) Filed: Apr. 28, 2022

(65) Prior Publication Data

US 2022/0347080 A1 Nov. 3, 2022

Related U.S. Application Data

(60) Provisional application No. 63/282,480, filed on Nov. 23, 2021, provisional application No. 63/222,322, filed on Jul. 15, 2021, provisional application No. 63/181,754, filed on Apr. 29, 2021, provisional application No. 63/181,735, filed on Apr. 29, 2021.

(51) Int. Cl.

| | |
|---|---|
| ***A61K 8/96*** | (2006.01) |
| ***A46B 3/00*** | (2006.01) |
| ***A46B 5/00*** | (2006.01) |
| ***A46B 9/00*** | (2006.01) |
| ***A46B 13/02*** | (2006.01) |
| ***A61C 3/06*** | (2006.01) |
| ***A61C 17/00*** | (2006.01) |
| ***A61K 8/19*** | (2006.01) |
| ***A61K 8/21*** | (2006.01) |
| ***A61K 8/24*** | (2006.01) |
| ***A61K 8/25*** | (2006.01) |
| ***A61K 8/29*** | (2006.01) |
| ***A61K 8/34*** | (2006.01) |
| ***A61K 8/9789*** | (2017.01) |
| ***A61Q 11/00*** | (2006.01) |

(52) U.S. Cl.

CPC .............. *A61K 8/965* (2013.01); *A46B 3/005* (2013.01); *A46B 5/0095* (2013.01); *A46B 9/005* (2013.01); *A46B 13/02* (2013.01); *A61C 3/06* (2013.01); *A61C 17/005* (2013.01); *A61K 8/19* (2013.01); *A61K 8/21* (2013.01); *A61K 8/24* (2013.01); *A61K 8/25* (2013.01); *A61K 8/29* (2013.01); *A61K 8/345* (2013.01); *A61K 8/9789* (2017.08); *A61Q 11/00* (2013.01); *A46B 2200/1066* (2013.01); *A61K 2800/28* (2013.01); *A61K 2800/87* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 3,621,577 A | 11/1971 | Spinello | | |
| 3,727,315 A | 4/1973 | Spinello | | |
| 5,316,475 A | 5/1994 | Rosenberg | | |
| 5,797,744 A | 8/1998 | Rosenberg | | |
| 12,226,518 B2 | 2/2025 | Kerr | | |
| 2007/0140986 A1 * | 6/2007 | Principe | ................ | A61Q 11/00 424/49 |
| 2012/0034575 A1 | 2/2012 | Tarr | | |
| 2014/0255490 A1 | 9/2014 | Lubbe et al. | | |
| 2016/0228341 A1 | 8/2016 | Lucas et al. | | |
| 2016/0331495 A1 | 11/2016 | Shokoohi | | |
| 2017/0202652 A1 | 7/2017 | Wang et al. | | |

FOREIGN PATENT DOCUMENTS

| | | | | | |
|---|---|---|---|---|---|
| CN | 212118328 U | 12/2020 | | |
| CN | 212118329 U | 12/2020 | | |
| DE | 102013004088 A1 * | 9/2014 | ........... | A61C 17/005 |
| WO | 9952395 A1 | 10/1999 | | |
| WO | WO 99/52395 | 10/1999 | | |
| WO | WO-2014185884 A1 * | 11/2014 | ........... | A61K 8/0204 |
| WO | WO 2021/067872 | 4/2021 | | |
| WO | WO-2021067872 A1 * | 4/2021 | ............. | A61K 8/027 |

OTHER PUBLICATIONS

English translation of DE-102013004088-A1. (Year: 2019).*
Office Action dated Apr. 8, 2024 issued in U.S. Appl. No. 17/732,030.
Search Report with Written Opinion dated Jul. 27, 2022 issued in International Patent Application PCT/US22/27003.
European Search Report dated Dec. 17, 2024 issued in the corresponding EP application.
Sylodent® 756, W. R. Grace & Co.—Conn., Jan. 1, 2008, 2 pages.
PCT/US22/27003, "Search Report with Written Opinion", PCT/US22/27003, Jul. 27, 2022, 13 pages.
22796825.2, "Supplementary European Search Report", 22796825.2, Dec. 17, 2024, 4 pages.

* cited by examiner

*Primary Examiner* — David J Blanchard
*Assistant Examiner* — Kaeleigh E Olsen
(74) *Attorney, Agent, or Firm* — Flaster Greenberg P.C.

(57) ABSTRACT

A meso-abrasive dentifrice formulation of from 15 wt % to 30 wt % a first abrasive, from 10 wt % to 15 wt % a second abrasive, and excipients. The second abrasive is silica and is different from the first abrasive. A system is also disclosed for cleaning a human oral cavity having the disclosed meso-abrasive dentifrice formulation and an oscillating cup for delivery of the dentifrice formulation. The system demonstrates a Cleaning Efficiency Index (CEI) of from 2.34 to 2.45. The system demonstrates an Increase in Gloss Score of greater than 28 and a system Relative Dentin Abrasiveness (RDA) value less than 100.

18 Claims, 3 Drawing Sheets

MESO-ABRASIVE DENTIFRICE AND SYSTEM FOR USING SAME

PRIORITY

This application is related to and claims priority to U.S. Provisional Patent Application No. 63/181,735 filed Apr. 29, 2021, 63/181,754 filed Apr. 29, 2021, 63/222,322 filed Jul. 15, 2021, and 63/282,480 filed Nov. 23, 2021, which are incorporated herein by reference. This application is filed concurrently with with U.S. patent application Ser. No. 17/732,030 filed Apr. 28, 2022, which is also incorporated herein by reference.

FIELD OF THE INVENTION

The present disclosure relates generally to dentifrice formulations, such as oral polishing pastes, that are effectively abrasive while having lower RDA values than conventional pastes, in other words, the inventive formulations are safer. In particular, the present disclosure relates to meso-abrasive dentifrice formulations including a silica abrasive and systems for using the dentifrice formulation in combination with an oscillating cup for delivery to the oral cavity.

BACKGROUND OF THE INVENTION

There is an ongoing interest in safe and effective formulations for dental hygiene. Cleaning and polishing of teeth is one of the primary desired benefits of dental brushing by consumers and coronal polishing performed by dental professionals. Generally, the cleaning and polishing is accomplished through abrasive dentifrices. For consumers, this dentifrice is commonly known as toothpaste and applied with a bristle brush. For coronal polishing, the dentifrice is known as "prophy paste" and is applied with a spinning (500-3500 RPM) rubber cup known as a "prophy cup" or a "prophy angle". Prophy paste is generally more effective at polishing since it is much more abrasive, commonly utilizing pumice as its primary abrasive media. Since it is applied by a professional, typically twice per year, its high abrasiveness does not result in excessive damage to dentition. However, this level of abrasiveness would be unacceptable in the hands of a consumer for daily use.

The abrasiveness of toothpastes used daily by consumers is measured on a scale called Relative Dentin Abrasiveness (RDA). It is a relative scale whereby 100 is the reference value for a standardized ADA/ISO slurry. The generally recognized maximum abrasiveness has an RDA value of from about 200 to 250. Abrasiveness beyond RDA 250 is not considered safe for consumer use since it can damage dental structures, in particular the softer dentin material.

The invention described herein satisfies a long-felt need for a more effective dentifrice that is safe for daily use, in particular a meso-abrasive dentifrice formulation. The meso-abrasive dentifrice formulation may be used with existing toothbrushes, manual or electric, or in combination with an inventive oscillating cup for delivery of the dentifrice to the oral cavity.

SUMMARY OF THE INVENTION

In some cases, the present disclosure relates to a meso-abrasive dentifrice formulation comprising from 15 wt % to 30 wt % a first abrasive and from 10 wt % to 15 wt % a second abrasive. The second abrasive is different from the first abrasive. The second abrasive is silica. Weight % is based upon the total weight of the formulation.

The meso-abrasive dentifrice formulation may comprise 12 wt % of the second abrasive. The second abrasive may be amorphous silica.

The meso-abrasive dentifrice formulation may comprise from 20 wt % to 25 wt % of the first abrasive. The first abrasive may be pumice having an FF grade. The first abrasive may include a first pumice having an FF grade and a second pumice having an ½ grade. The first abrasive may include 5 wt % of the second pumice having an ½ grade.

The meso-abrasive dentifrice formulation may include from 40 wt % to 50 wt % glycerin based upon the total weight of the formulation. The meso-abrasive dentifrice formulation may include from 5 wt % to 15 wt % purified water based upon the total weight of the formulation. The meso-abrasive dentifrice formulation may include at least one of sodium fluoride, calcium acetate, dibasic sodium phosphate, or combinations thereof in an amount totaling less than 10 wt %.

The meso-abrasive dentifrice formulation may comprise:

from 15 wt % to 30 wt % a first abrasive, wherein the first abrasive is pumice selected from a first pumice of FF grade, a second pumice of ½ grade, or combinations thereof;

from 10 wt % to 15 wt % a second abrasive, wherein the second abrasive is amorphous silica;

from 40 wt % to 50 wt % glycerin;

from 5 wt % to 15 wt % purified water; and from 5 wt % to 15 wt % additional ingredients, wherein wt % is based upon the total weight of the formulation.

In some cases, the present disclosure relates to a system for cleaning a human oral cavity comprising the meso-abrasive dentifrice formulation according to any of the above paragraphs and an oscillating cup for delivery of the dentifrice formulation.

The oscillating cup may be an oscillating rubber cup. The oscillating cup may oscillate reciprocally at an angle less than 360 degrees. The oscillating cup may oscillate reciprocally at an angle of from 45 degrees to 90 degrees. The oscillating cup may oscillate reciprocally at a speed of from 4000 times per minute to 11,000 times per minute. The oscillating cup may oscillate reciprocally at a speed of 8000 times per minute. The oscillating cup may oscillate reciprocally at a speed of 9000 times per minute.

The system may demonstrate at least one of:

a system Relative Dentin Abrasiveness (RDA) value less than 100;

a Pellicle Cleaning Ratio (PCR) value of greater than 125; and a Cleaning Efficiency Index (CEI) of greater than 2.00.

The system may demonstrate a Cleaning Efficiency Index (CEI) of from 2.34 to 2.45.

The system may demonstrate an Increase in Gloss Score of greater than 28 and a system Relative Dentin Abrasiveness (RDA) value less than 100.

DETAILED DESCRIPTION OF THE PRESENTLY PREFERRED EMBODIMENTS

Introduction

Figure 1:
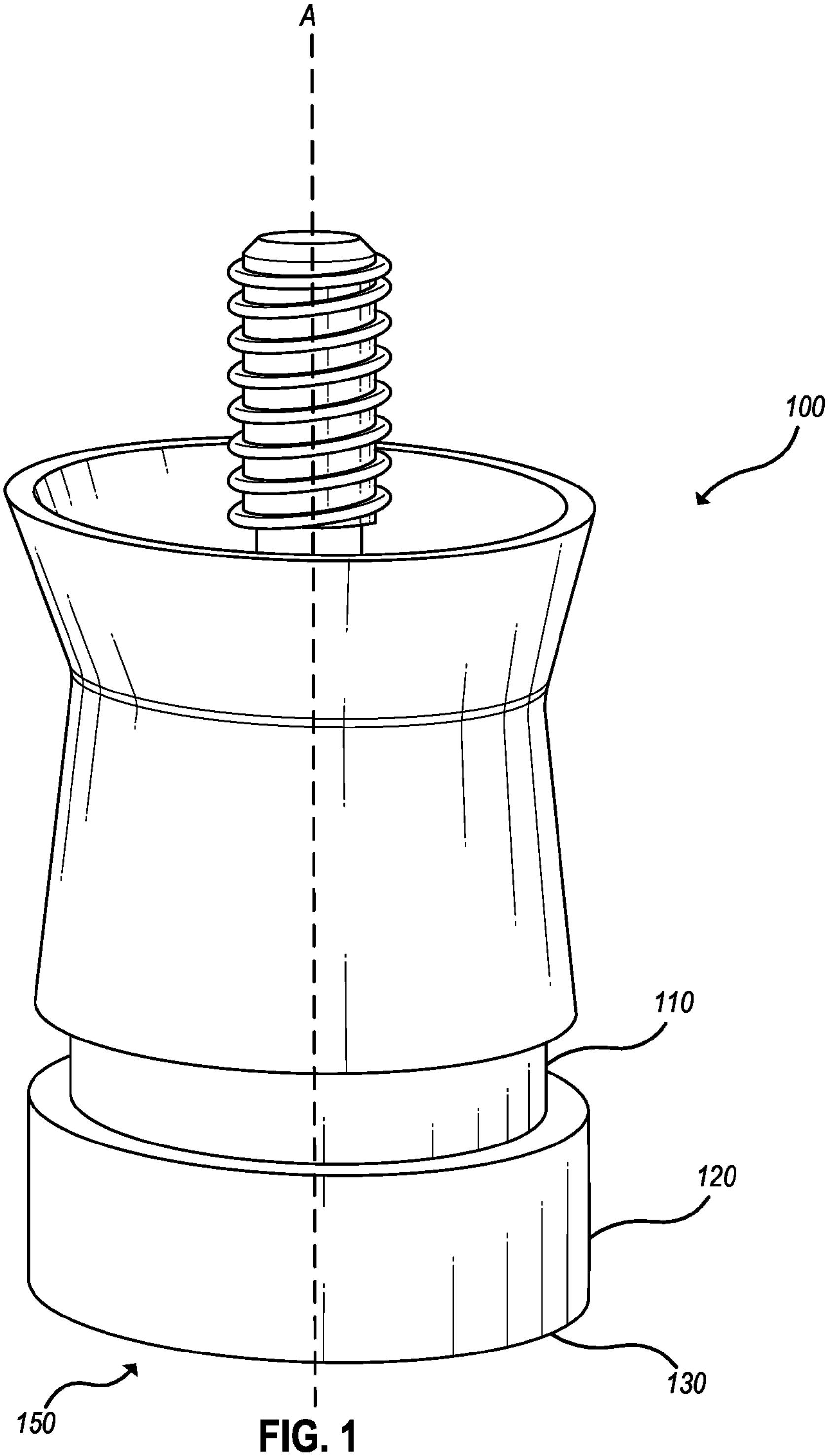
FIG. 1 illustrates an oscillating cup, according to an exemplary embodiment.

As noted above, it is generally recognized that conventional pastes should have maximum abrasiveness not to exceed RDA values of 200 to 250, above which is an unsafe level of abrasiveness. For example, many conventional prophy pastes typically rely on pumice as the major component to achieve adequate abrasiveness. However, a paste using less pumice that is at least as effective while also being safer is needed.

Moreover, the invention disclosed herein also relates to a system for dental cleaning and polishing that is simultaneously high in cleaning effectiveness and relatively low in abrasion. This allows the system to have superior cleaning performance and also be safe enough for daily consumer use. Cleaning effectiveness is commonly measured as the Pellicle Cleaning Ratio (PCR) and the safety is measured as RDA. The combined value is known as the Cleaning Effectiveness Index (CEI) which takes into account both the ability to clean along with the overall abrasion. A high CEI means that it is effective at cleaning and low in abrasion. The performance of state of the art toothpaste is well summarized by Schemehorn et al. [See e.g., Schemehorn, B. R., *Abrasion, Polishing, and Stain Removal Characteristics of Various Commercial Dentifrices In Vitro*, The Journal of Clinical Dentistry, Vol. XXII, No. 1, pp. 11-18], which is incorporated herein by reference.]

The inventors have now found that a dentifrice having a synergistic combination of pumice (not typically found in consumer paste due to safety) and further including silica that provides superior cleaning effectiveness relative to consumer toothpastes with an RDA value safe for daily consumer use. Further, the present invention addresses unmet professional and consumer needs by providing a system of a synergistic combination of dentifrice and oscillating cup to yield results not otherwise achievable using conventional pastes and/or electric oral hygiene appliances.

As used herein and in the appended claims, the use of "a," "an," and/or "the" is intended to include both the singular and plural (e.g., "one or more") unless the context clearly dictates otherwise. Thus, for example, reference to a "pumice" is a reference to one or more pumices and equivalents thereof known to those skilled in the art, and so forth.

Unless specified, "%" may refer to a percent by weight percent, or a percent by volume, or a percent weight by unit volume, and the relevant units would be immediately apparent to one of ordinary skill in the art based on the context.

As used herein, "greater than" and "less than" limits may also include the number associated therewith. Stated another way, "greater than" and "less than" may be interpreted as "greater than or equal to" and "less than or equal to." It is contemplated that this language may be subsequently modified in the claims to include "or equal to." For example, "greater than 4.0" may be interpreted as, and subsequently modified in the claims as "greater than or equal to 4.0."

The meso-abrasive dentifrice formulations are so-named "meso-abrasive" because the resultant abrasiveness is in between the abrasiveness of a consumer toothpaste and professional prophy paste. These formulations achieve this by combining a limited amount of pumice (the abrasive used in prophy paste) with abrasives used in consumer toothpastes.

Meso-abrasive dentifrice formulations as described herein may be used with a system, also described herein, having an oscillating cup. The system includes where the cup oscillates reciprocally meaning the cup moves back and forth in a reciprocating action.

Meso-Abrasive Dentifrice Formulation. The meso-abrasive dentifrice formulations disclosed herein include first and second abrasives. In particular, the first abrasive may be a pumice suitable for dental cleaning and the second abrasive may be silica. The formulations may include other ingredients as will be discussed such as excipients as carrier vehicle for the paste. Notably, the disclosed formulations have pumice as a minor component (less than 50 wt % of the total formulation) whereas conventional pastes typically require higher loadings of pumice, e.g., greater than 50 wt % of the formulation.

Pumice may be of any suitable pumice for dental compounds and finishing. Pumice is amorphous aluminum silicate and may be a naturally calcined volcanic glass foam characterized by highly vesicular strands permeated with tiny air bubbles.

In some embodiments, the pumice includes one or more pumices characterized as having different grades. The grades for pumice are determined by particle size specification, such as by Hess Pumice Grades for example. Pumice of Grade FF may be referred to herein as 'fine pumice' and pumice of Grade ½ may be referred to herein as 'coarse pumice'. Grade designations contemplated in the formulations used herein include Hess Grades -325, FFFF, FFF, FF, F, 1/0, 2/0, 3/0, 0, 0 1/2, 0 3/4, ½, 1½, or combinations thereof.

Pumice of FF grade, as is suitable in the disclosed meso-abrasive dentifrice formulations, has a particle size specification of Grade FF. Grade FF means that 99.5%-100% of the particles pass through a US 140 Mesh (openings of 106 micron or 0.106 mm), 95%-100% of the particles pass through a US 170 Mesh (openings of 90 micron or 0.09 mm), 86%-98% of the particles pass through a US 200 Mesh (openings of 75 micron or 0.075 mm), and 63%-77% of the particles pass through a US 325 Mesh (openings of 45 micron or 0.045 mm).

Alternatively, or in addition to, pumice of ½ grade is suitable in the disclosed meso-abrasive dentifrice formulations and has a particle size specification designation of Grade ½. Grade ½ means that 99.5%-100% of the particles pass through a US 50 Mesh (openings of 300 micron or 0.3 mm), 70%-80% of the particles pass through a US 60 Mesh (openings of 250 micron or 0.25 mm), 4%-16% of the particles pass through a US 80 Mesh (openings of 180 micron or 0.18 mm), 0%-8% of the particles pass through a US 100 Mesh (openings of 150 micron or 0.15 mm), and 0%-4% of the particles pass through a US 200 Mesh (openings of 75 micron or 0.075 mm).

The meso-abrasive dentifrice formulations include silica. The silica may be included as a second abrasive, which is different from the first abrasive. In some embodiments, the first abrasive is pumice and the second abrasive is silica and together the first and second abrasives represent a minor component, e.g., less than 50 wt % of the total formulation.

The silica may be amorphous silica. Specifically, the silica may be a synthetic, amorphous silica appearing as a fine white powder that is taste and odor free. The particle size of the silica may be in a range of from 0.5 microns to 250 microns. In one embodiment, the meso-abrasive dentifrice formulation comprises silica having a particle size ranging from 0.5 microns to 250 microns, e.g., from 1.0 microns to 100 microns, or from 5 microns to 25 microns. In some preferred embodiments, the meso-abrasive dentifrice formulation includes silica having a particle size from 5 microns to 25 microns. In other preferred embodiments, the meso-abrasive dentifrice formulation includes silica having a particle size from 8 microns to 20 microns. Sylodent® 756 is a safe, suitable commercially available amorphous silica useful in the disclosed meso-abrasive dentifrice formulations.

The meso-abrasive dentifrice formulations may comprise first and second abrasives. In one embodiment, the meso-abrasive dentifrice formulation comprises a first abrasive, e.g., pumice, in an amount ranging from 15 wt % to 30 wt % based upon the total weight of the formulation, e.g., from 18 wt % to 27 wt %, from 20 wt % to 25 wt %, or from 22 wt % to 23 wt %. In terms of lower limits, the meso-abrasive dentifrice formulation may comprise greater than 15 wt % of a first abrasive, e.g., greater than 18 wt %, greater than 20 wt %, or greater than 22 wt % based upon the total weight of the formulation. In terms of upper limits, the meso-abrasive dentifrice formulation may comprise less than 30 wt % of a first abrasive, e.g., less than 27 wt %, less than 25 wt %, or less than 23 wt % based upon the total weight of the formulation. The formulation may comprise from 20 wt % to 25 wt % of the first abrasive. In some preferred embodiments, the meso-abrasive dentifrice formulation includes 22.7 wt % of the first abrasive, e.g., pumice.

The first abrasive of the meso-abrasive dentifrice formulation may include one or more pumices characterized by one or more grades. In some embodiments, the meso-abrasive dentifrice formulation includes where the first abrasive includes a first pumice having an FF grade, a second pumice having an ½ grade, or combinations thereof. In some embodiments, the first abrasive present in the amounts detailed above where 5 wt % (based upon the total weight of the formulation) of the first abrasive is the second pumice having an ½ grade with the balance of the first abrasive being the first pumice having an FF grade.

In one embodiment, the meso-abrasive dentifrice formulation comprises a second abrasive, e.g., silica, in an amount ranging from 10 wt % to 15 wt % based upon the total weight of the formulation, e.g., from 11 wt % to 14 wt %, from 11 wt % to 13 wt %, or from 11.5 wt % to 12.5 wt %. In terms of lower limits, the meso-abrasive dentifrice formulation may comprise greater than 10 wt % of a second abrasive, e.g., greater than 11 wt %, or greater than 11.5 wt % based upon the total weight of the formulation. In terms of upper limits, the meso-abrasive dentifrice formulation may comprise less than 15 wt % of a second abrasive, e.g., less than 14 wt %, less than 13 wt %, or less than 12.5 wt % based upon the total weight of the formulation. In some preferred embodiments, the meso-abrasive dentifrice formulation includes 12 wt % of the second abrasive, e.g., silica.

Additional Ingredients.

The meso-abrasive dentifrice formulations include additional ingredients that together (in sum) comprise a major component of the formulation, e.g., greater than 50 wt % based upon the total weight of the formulation. These ingredients include excipients (vehicle carrier ingredients) chosen from one or more of glycerin and purified water. Other excipients may include thickeners, suspension stabilizers, emulsion stabilizers, and/or dispersants. In some embodiments, the meso-abrasive dentifrice formulations include Xanthan gum, Cekol® 2000, Veegum®, or combinations thereof. Additional ingredients also include those to provide flavor, color, sweetness, and health and/or whitening effects. Additional ingredients may include sodium fluoride, calcium acetate, and dibasic sodium phosphate, among others. In one embodiment, the meso-abrasive dentifrice formulation comprises excipients, e.g., glycerin and/or purified water.

The meso-abrasive dentifrice formulations may comprise glycerin in an amount ranging from 40 wt % to 50 wt % based upon the total weight of the formulation, e.g., from 42 wt % to 48 wt %, from 43 wt % to 47 wt %, or from 44 wt % to 46 wt %. In terms of lower limits, the meso-abrasive dentifrice formulation may comprise greater than 40 wt % of glycerin, e.g., greater than 42 wt %, greater than 43 wt %, or greater than 44 wt % based upon the total weight of the formulation. In terms of upper limits, the meso-abrasive dentifrice formulation may comprise less than 50 wt % of glycerin, e.g., less than 48 wt %, less than 47 wt %, or less than 46 wt % based upon the total weight of the formulation. The formulations may comprise from 44 to 46 wt % of glycerin. In some preferred embodiments, the meso-abrasive dentifrice formulation includes 45.6 wt % glycerin.

The meso-abrasive dentifrice formulations may comprise water, e.g., purified water, in an amount ranging from 5 wt % to 15 wt % based upon the total weight of the formulation, e.g., from 7 wt % to 13 wt %, from 8 wt % to 12 wt %, or from 9 wt % to 11 wt %. In terms of lower limits, the meso-abrasive dentifrice formulation may comprise greater than 5 wt % of purified water, e.g., greater than 7 wt %, greater than 8 wt %, or greater than 9 wt % based upon the total weight of the formulation. In terms of upper limits, the meso-abrasive dentifrice formulation may comprise less than 15 wt % of purified water, e.g., less than 13 wt %, less than 12 wt %, or less than 11 wt % based upon the total weight of the formulation. In some preferred embodiments, the meso-abrasive dentifrice formulation includes 10 wt % water.

The meso-abrasive dentifrice formulations may comprise total excipients, e.g., glycerin and/or purified water, in an amount ranging from 45 to 65 wt % based upon the total weight of the formulation, e.g., from 45 wt % to 60 wt %, from 50 wt % to 65 wt %, or from 45 wt % to 55 wt %. In terms of lower limits, the meso-abrasive dentifrice formulation may comprise greater than 45 wt % of excipients, e.g., greater than 50 wt % based upon the total weight of the formulation. In terms of upper limits, the meso-abrasive dentifrice formulation may comprise less than 65 wt % of excipients, e.g., less than 60 wt %, or less than 55 wt % based upon the total weight of the formulation. In some preferred embodiments, the meso-abrasive dentifrice formulation includes 54 wt % to 64 wt % glycerin, purified water, or combinations thereof.

Other than the first and second abrasives as described along with excipients, such as glycerin and/or purified water, the meso-abrasive dentifrice formulation may comprise additional ingredients for flavor, coloring, sweetness, health and/or whitening. These additional ingredients may be chosen from, but not limited to, Sodium Fluoride USP, Calcium Acetate (anhydrous), Dibasic Sodium Phosphate, Potassium Sorbate NF, Flavor Spearmint Oil, Xanthan gum, Cekol® 2000, Veegum®, Sodium Benzoate USP, Titanium Dioxide, Stevia Extract Powder (97%), or combinations thereof. These additional ingredients are included in amounts totaling less than 10 wt % based upon the total weight of the formulation.

The meso-abrasive dentifrice formulations may comprise total additional ingredients, e.g., additional ingredients excluding first abrasives, second abrasives, and excipients, in an amount ranging from 5 wt % to 15 wt % based upon the total weight of the formulation, e.g., from 7 wt % to 13 wt %, from 8 wt % to 12 wt %, or from 9 wt % to 11 wt %. In terms of lower limits, the meso-abrasive dentifrice formulation may comprise greater than 5 wt % of additional ingredients, e.g., greater than 7 wt %, greater than 8 wt %, or greater than 9 wt % based upon the total weight of the formulation. In terms of upper limits, the meso-abrasive dentifrice formulation may comprise less than 15 wt % of additional ingredients, e.g., less than 13 wt %, less than 12 wt %, or less than 11 wt % based upon the total weight of the formulation. In some preferred embodiments, the meso-abrasive dentifrice formulation includes less than 10 wt % additional ingredients chosen from, but not limited to, Sodium Fluoride USP, Calcium Acetate (anhydrous), Dibasic Sodium Phosphate, Potassium Sorbate NF, Flavor Spearmint Oil, Xanthan gum, Cekol® 2000, Veegum®, Sodium Benzoate USP, Titanium Dioxide, Stevia Extract Powder (97%), or combinations thereof.

Exemplary Formulations

In one embodiment, a meso-abrasive dentifrice formulation comprises:

from 15 wt % to 30 wt % a first abrasive, and,
from 10 wt % to 15 wt % a second abrasive different from the first abrasive,
wherein the second abrasive is silica, and
wherein wt % is based upon the total weight of the formulation.

In another embodiment, the meso-abrasive dentifrice formulation comprises:

from 15 wt % to 30 wt % a first abrasive, wherein the first abrasive is pumice selected from a first pumice of FF grade, a second pumice of ½ grade, or combinations thereof;
from 10 wt % to 15 wt % a second abrasive, wherein the second abrasive is amorphous silica;
from 40 wt % to 50 wt % glycerin;
from 5 wt % to 15 wt % purified water; and
from 5 wt % to 15 wt % additional ingredients,
wherein wt % is based upon the total weight of the formulation.

Dentifrice for Use With System Including Oscillating Cup.

While the dentifrice as described herein may be used with any suitable toothbrush, such as manual, or teeth cleaning device, such as electronic toothbrush systems, additional benefits are realized when the dentifrice of the invention is used with inventors' cleaning system having an oscillating cup. This system having an oscillating cup for cleaning a human oral cavity, teeth, and/or dentures is described in detail in co-pending with U.S. patent application Ser. No. 17/732,030, which is incorporated herein by reference.

Conventional dental prophy cups allow only limited off-axis tolerance, in other words, reduced contact with a tooth when the cup is positioned off from perpendicular to the tooth. The system herein includes an oscillating cup 100, as shown in FIG. 1, having distal annular groove 110, distal portion 120, and distal edge 130 defining inner cavity 150. The distal annular groove 110 provides for articulation and/or contourability of the cup to provide a greater contact surface of the cup with for example a tooth, even with off-axis positioning. The cup oscillates reciprocally about axis A.

Figure 2:
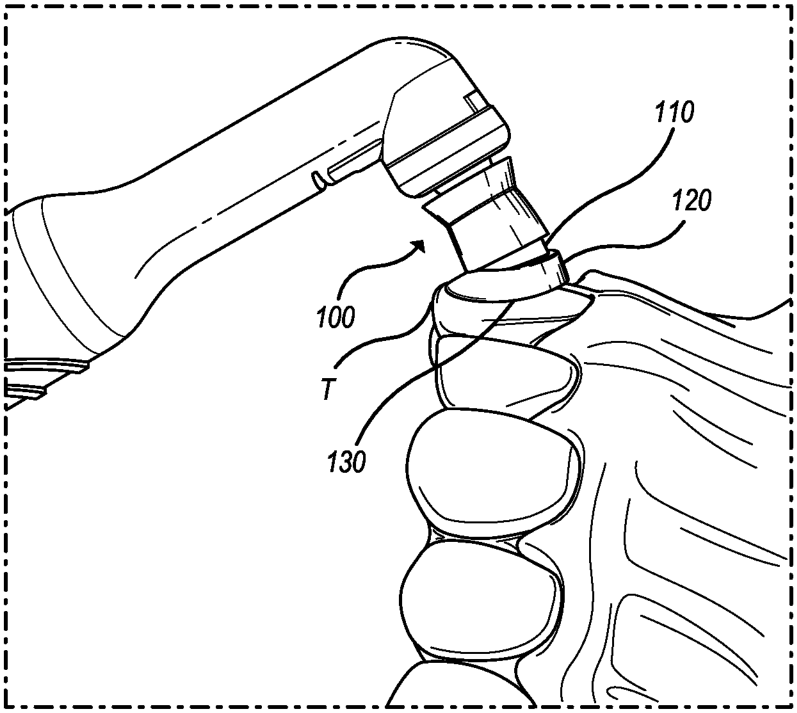
FIG. 2 illustrates the oscillating cup according to FIG. 1 in an oral cavity, according an exemplary embodiment.
Figure 3:
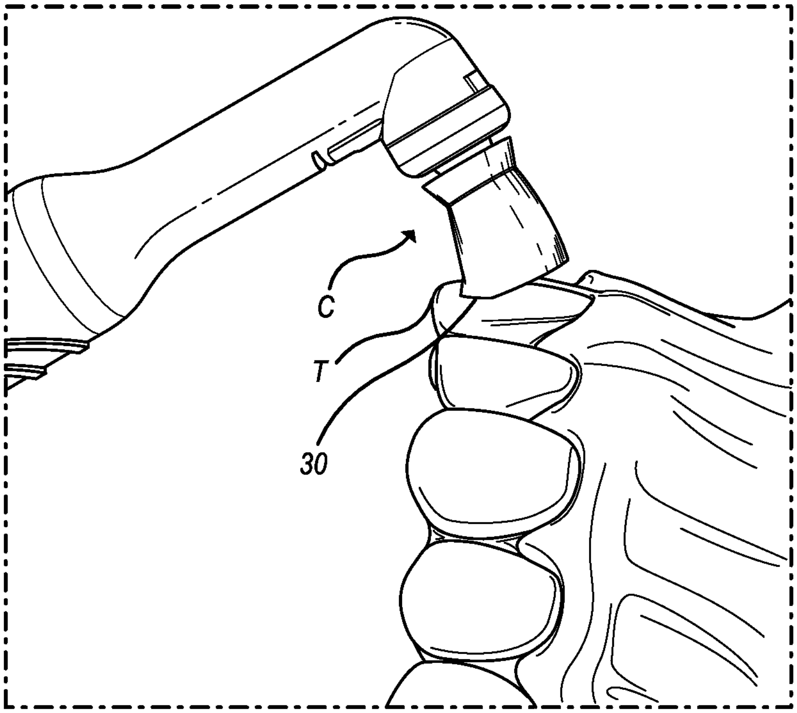
FIG. 3 illustrates a conventional prophy cup in an oral cavity.
Figure 4:
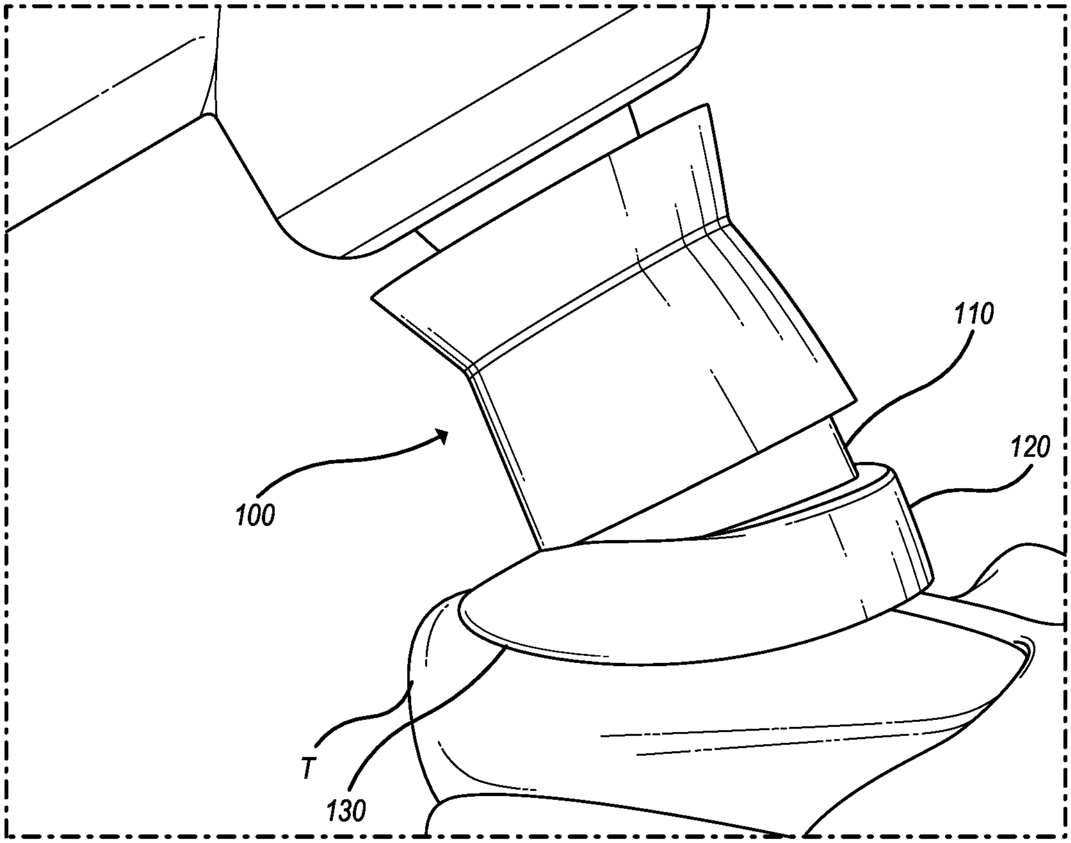
FIG. 4 illustrates the oscillating cup according to FIGS. 1 and 2 in contact with a tooth, according an exemplary embodiment.

As shown in FIG. 2, oscillating cup 100 has distal annular groove 110 to provide for the cup to articulate, contour, and flare as shown in FIG. 2. Cup 100 provides for a greater contact area of the distal portion 120 having distal edge 130 in contact with the surface of tooth T, as shown in FIGS. 2 and 4 in closer detail. This is in contrast with the limited contact that edge 30 of convention cup C has with tooth T, as shown in FIG. 3. Conventional cup C does not have a distal annular groove. The oscillating cup has two distinct advantages over conventional prophy cups. Firstly, the oscillating cup 100 having distal annular groove 110 can contour to a tight radius (R2.4 mm). With downward force, the edge 130 of cup 100 then wraps around the tight radius to completely adapt to the radius, which translates into greater surface contact when applied to, for example, a tooth within an oral cavity. Secondly, distal annular groove 110 allows for the ability of the cup to flare to access the interproximal areas and reach the gingival and subgingival margins. As compared with a control (conventional prophy cup), the oscillating cup has 330% more flaring ability.

In some aspects, the system having oscillating cup as described is used in combination with the meso-abrasive dentifrice formulation. The system including the oscillating cup combines synergistically with the meso-abrasive dentifrice formulation to provide superior cleaning and safety as compared with conventional systems with conventional dentifrice formulations.

The oscillating cup of the system is configured to hold an appropriate amount of dentifrice, e.g., from 25 mg to 150 mg, in cup inner cavity 150. In one embodiment, the cup inner cavity holds 85 mg of the meso-abrasive dentifrice formulation. The oscillating cup with the dentifrice is then contacted to the oral cavity teeth and/or gums for cleaning, for example, as illustrated in FIG. 2 demonstrating a contact surface with tooth T all along edge 130 of cup 100.

The oscillating cup may be made of any suitable material that is safe for contact with human oral cavities such as, for example, elastomers. Examples of suitable elastomers include natural and synthetic rubbers, silicone elastomers, nitrile rubbers, ethylene propylene diene rubbers, neoprene rubbers, thermoplastic elastomers, and combinations thereof.

The oscillating cup 100 of the system oscillates reciprocally about axis A as shown in FIG. 1. Importantly, the oscillating cup of the system oscillates reciprocally (back and forth) at an angle less than 360 degrees, in other words, less than a full rotation before reversing direction about axis A. This is an important distinction from conventional electric toothbrushes that spin continuously in the same direction in full (360 degrees) rotation and do not change direction. It is believed that cleaning is enhanced due to the reciprocating action of the oscillating cup. This reciprocating action also reduces the abrasion potential of the dentifrice thus aiding the meso-abrasive dentifrice formulation to be safely used by a consumer. The oscillating cup oscillates reciprocally about axis A at an angle ranging from 45 degrees to 315 degrees, from 45 degrees to 270 degrees, from 45 degrees to 225 degrees, from 45 degrees to 180 degrees, from 45 degrees to 135 degrees, or from 45 degrees to 90 degrees. In some preferred embodiments, the oscillating cup oscillates reciprocally about axis A at an angle of from 45 degrees to 90 degrees.

The oscillating cup of the system oscillates reciprocally at a speed of from 4000 times per minute to 11,000 times per minute. This is an important distinction from conventional electric toothbrushes that spin at a speed full rotations at from 500 revolutions per minute to 3500 revolutions per minute. It is believed that cleaning is enhanced due to the high speed reciprocating action of the oscillating cup. The oscillating cup oscillates reciprocally at a speed from 4000 times per minute to 11,000 times per minute, e.g., from 5000 times per minute to 10,000 times per minute, or from 7000 times per minute to 9000 times per minute. In some preferred embodiments, the oscillating cup oscillates reciprocally at a speed of 8000 times per minute. In other preferred embodiments, the oscillating cup oscillates reciprocally at a speed of 9000 times per minute.

Advantageously, the system having the dentifrice and oscillating cup as described demonstrates at least one of: a Prophy Polishing Dentin Abrasion (PPDA) value less than 125; a Relative Dentin Abrasiveness (RDA) value less than 100; a Pellicle Cleaning Ratio (PCR) value of greater than 125; and a Cleaning Efficiency Index (CEI) of greater than 2.00. In some embodiments, the system having the dentifrice and oscillating cup as described demonstrates each of these: a Prophy Polishing Dentin Abrasion (PPDA) value less than 125; a Relative Dentin Abrasiveness (RDA) value less than 100; a Pellicle Cleaning Ratio (PCR) value of greater than 125; and a Cleaning Efficiency Index (CEI) of greater than 2.00.

In some embodiments, the system having the dentifrice and oscillating cup demonstrates a Cleaning Efficiency Index (CEI) of from 2.34 to 2.45.

In some embodiments, the system having the dentifrice and oscillating cup demonstrates an Increase in Gloss Score of greater than 28 and a Relative Dentin Abrasiveness (RDA) value less than 100.

Because the oscillating cup provides articulating and conforming features as described, they are desirable and suitable for trained (dental professionals) and less trained (consumers) alike for performing polishing on patients or as a consumer self-care product, respectively. The off axis tolerance means that the user does not have to be perfectly perpendicular to tooth to achieve safe and effective polishing. This is not achievable with a conventional product, because a novice user trying to manipulate the device by mirror reflection, rather than direct sight, is generally unable to maintain positioning of the cup perpendicular to the tooth surface at all times as required for conventional prophy cups.

EXAMPLES

Meso-Abrasive Dentifrice Formulations Ex. A and Ex. B. The meso-abrasive dentifrice formulations Example A (Ex. A) and Example B (Ex. B) were prepared according to Table 1 below. Also shown on Table 1 is Comparative 1 (C1), which is the least abrasive commercially available prophy paste manufactured by Premier Dental (Enamel Pro Prophy Paste [EPPP], Fine). Ex. A and Ex. B each contain significantly less pumice at a total of 22.70 wt % pumice as compared with C1 having about twice as much pumice at 44.00 wt %. Additionally, Ex. A and Ex. B contain silica (Sylodent® 756, amorphous silica), and C1 contains zero silica.

Table 1 shows the composition of formulations by weight % for Example A, Example B, and Comparative 1.

TABLE 1

| Composition of Formulations by Weight % | | | |
|---|---|---|---|
| Ingredient | Example A (Ex. A) | Example B (Ex. B) | Comparative 1 (C1) |
| Glycerin, USP | 45.57 | 45.57 | 32.31 |
| Purified Water, USP | 10.00 | 10.00 | 9.24 |
| Pumice, Grade FF | 22.70 | 17.70 | 44.00 |
| Pumice, Grade ½ | N/A | 5.00 | N/A |
| Silica | 12.00 | 12.00 | N/A |
| Sodium Fluoride, USP | 0.25 | 0.25 | 2.72 |

TABLE 1-continued

| Composition of Formulations by Weight % | | | |
|---|---|---|---|
| Ingredient | Example A (Ex. A) | Example B (Ex. B) | Comparative 1 (C1) |
| Calcium Acetate Anhydrous | 3.00 | 3.00 | 3.00 |
| Dibasic Sodium Phosphate | 1.75 | 1.75 | 1.75 |
| Potassium Sorbate NF | 0.40 | 0.40 | 0.20 |
| Flavor Spearmint Oil | 0.30 | 0.30 | 0.30 |
| Xanthan Gum | 0.50 | 0.50 | N/A |
| Cekol ® 2000 | 0.50 | 0.50 | N/A |
| Veegum ® | 2.00 | 2.00 | N/A |
| Sodium Benzoate USP | 0.08 | 0.08 | N/A |
| Titanium Dioxide | 0.80 | 0.80 | 1.60 |
| Stevia Extract Powder 97% | 0.15 | 0.15 | N/A |
| sodium silicate | N/A | N/A | 3.00 |
| agar | N/A | N/A | 0.40 |
| Sucralose powder | N/A | N/A | 0.08 |
| peppermint oil | N/A | N/A | 0.20 |
| Phosphoric acid | N/A | N/A | 1.20 |
| Total | 100.00 | 100.00 | 100.00 |

The formulations were tested with systems having an oscillating cup as disclosed herein, and the oscillating cup was made of rubber. The oscillating cup of the system oscillated reciprocally at an angle ranging from 45 degrees to 90 degrees at a speed of about 8000 times per minute. The oscillating cup system included a battery powered consumer toothbrush handle.

Prophy Polishing Dentin Abrasion (PPDA). Ex. A formulation was tested using the system having oscillating cup and the values for Prophy Polishing Dentin Abrasion (PPDA) are shown in Table 2. PPDA is similar to RDA, but is on a different scale and uses a pumice slurry as the reference material. A lower PPDA value means less abrasive as compared with higher values. PPDA values are determined using a standard test as described below. For Ex. A using the system with oscillating cup as described herein, the PPDA values are determined using the standard test except that the oscillating cup as described herein has replaced the Young Webbed-Soft-Gray prophy cup. Thus the PPDA value for "Ex. A/System with oscillating cup" may be referred to as "system PPDA".

Ex. A formulation was also tested using the standard test for determining PPDA including a conventional prophy cup that spins (fully rotating) at a speed of 1500 RPM in a portable prophylaxis testing machine equipped with a Young Webbed-Soft-Gray prophy cup as was comparative formulation C1. As shown in Table 2, the relative reduction in abrasion of Ex. A vs C1 is significant as is the relative effect of the oscillating cup vs a spinning cup.

TABLE 2

| Prophy Polishing Dentin Abrasion (PPDA) Values | |
|---|---|
| Ex. A/System with oscillating cup | 111.28 ± 11.88 |
| Ex. A/System with conventional spinning cup | 254.99 ± 13.39 |
| C1/System with conventional spinning cup | 646.82 ± 43.87 |

Using systems having conventional prophy spinning cups according to the standard test for determining PPDA, the formulation of Ex. A was found to be significantly less abrasive with a PPDA value of 255 as compared with conventional C1 prophy paste with a PPDA value of 647. Ex. B was also found to be less abrasive than conventional prophy paste.

Further, the formulation of Ex. A using the system with oscillating cup was found to be significantly less abrasive than the same formulation using the system with a conventional spinning cup, reducing the PPDA value from 255 to a system PPDA value of 111.

Relative Dentin Abrasiveness (RDA). Formulations according to Ex. A and Ex. B were tested using manual brushes according to the standard test for determining values for Relative Dentin Abrasiveness (RDA), which are shown in Table 3. Ex. A and Ex. B are herein designated as meso-abrasive because the RDA values measured above 250. For reference, ISO/ADA reference toothbrush and paste provides an RDA of 100.

TABLE 3

| Relative Dentin Abrasiveness (RDA) Values (Manual Brush) | |
|---|---|
| Ex. A/Manual Toothbrush | 310.08 ± 8.12 |
| Ex. B/Manual Toothbrush | 322.32 ± 7.51 |

Additional testing was performed to determine the "system RDA" values of formulations according to Ex. A and Ex. B used with the system having the oscillating cup disclosed herein with system RDA values shown in Table 4.

TABLE 4

| System Relative Dentin Abrasiveness (RDA) Values (Oscillating Cup System) | |
|---|---|
| Ex. A/System with oscillating cup | 59.88 ± 5.23 |
| Ex. B/System with oscillating cup | 72.16 ± 8.14 |

Thus, the oscillating cup system in combination with the meso-abrasive dentifrice formulation disclosed herein demonstrated system RDA values significantly below 250, and even below 100, allowing for safe, regular use of the system/dentifrice combinations by a consumer.

Pellicle Cleaning Ratio (PCR). Cleaning effectiveness was also measured according to the Pellicle Cleaning Ratio (PCR) test with results shown in Table 5 for meso-abrasive dentifrice formulation used in combination with the oscillating cup system. A PCR value of at least 50 indicates acceptable cleaning power (extrinsic stain removal).

TABLE 5

| Pellicle Cleaning Ratio (PCR) Values | |
|---|---|
| Reference Paste/Manual Toothbrush | 100.0 ± 3.7 |
| Ex. A/System with oscillating cup | 130.0 ± 7.0 |
| C1/System with oscillating cup | 148.7 ± 6.1 |
| Ex. B/System with oscillating cup | 154.8 ± 4.5 |

Cleaning Efficiency Index (CEI). The above values for the RDA and PCR were then used to calculate the Cleaning Efficiency Index as in: $CEI=(RDA+PCR-50)/RDA$. CEI emphasizes the importance of good stain removal properties and low dentin abrasivity. [See e.g., Schemehorn et. al., J. of Clinical Dentistry, 2011, Vol. 22, No. 1, pp. 11-18.] CEI is an index used to rank cleaning performance while taking into account the abrasiveness, i.e., to indicate dental cleaning systems efficacy (cleaning) and safety (low abrasion). CEI for Ex. A and Ex. B are shown in Table 6 as is the value for a ISO/ADA Reference Toothbrush and Abrasive sample.

TABLE 6

| Cleaning Efficiency Index (CEI) Values | |
|---|---|
| ISO/ADA Reference | 1.50 |
| Ex. A/System with oscillating cup | 2.34 |
| Ex. B/System with oscillating cup | 2.45 |
| C2 Commercial Toothpaste/System | 1.80 |

CEI and PCR values for Ex. A and Ex. B as in Tables 5 and 6 were compared with known values for commercial pastes (as disclosed in Schemehorn referenced above). Surprisingly, both Ex. A (in combination with oscillating cup system) and Ex. B (in combination with oscillating cup system) clean as well or better than any commercial toothpaste (as measured in PCR), yet were also among the lowest in abrasiveness. This synergistic combination of an oscillating cup system and meso-abrasive dentifrice yielded a CEI of from 2.34 to 2.45 as shown in Table 6. For comparison, the highest CEI for commercial pastes (as disclosed in Schemehorn) was only approximately 1.80—far below that of Ex. A and Ex. B with oscillating cup systems.

Gloss Score. The ability to polish enamel for the oscillating cup system in combination with meso-abrasive dentifrices as disclosed herein were tested and Gloss Score determined, which is a measure of ability to produce a smooth shiny enamel surface. Results are shown in Table 7.

TABLE 7

| Gloss Score | | | | |
|---|---|---|---|---|
| Treatment | Maximum Attainable Gloss Score | Dulled Gloss Score | Post Treatment Gloss Score | Increase in Gloss Δ Gloss Score |
| Ex. A/System with oscillating cup | 117.1 ± 6.2 | 6.5 ± 1.6 | 34.8 ± 3.5 | 28.3 ± 2.1 |
| C1/System with oscillating cup | 122.4 ± 1.3 | 7.8 ± 2.2 | 44.0 ± 3.8 | 36.3 ± 5.2 |
| Ex. B/System with oscillating cup | 123.1 ± 2.9 | 5.1 ± 0.5 | 44.8 ± 4.4 | 39.6 ± 4.7 |
| ISO/ADA Reference Toothbrush and Abrasive | 119.8 ± 1.2 | 5.9 ± 1.6 | 45.8 ± 3.2 | 39.9 ± 4.1 |

A summary is shown in Table 8 comparing Ex. A (in combination with oscillating cup system) and Ex. B (in combination with oscillating cup system) with the ISO/ADA reference standard. Ex. B (in combination with oscillating cup system) was able to polish as effectively as the ISO/ADA reference manual toothbrush as shown in A Gloss Score. Ex. B (in combination with oscillating cup system) also demonstrated, importantly, a significantly lower RDA value indicating higher safety and a significantly higher CEI value indicating higher efficacy with safety.

TABLE 8

| Summary | | | |
|---|---|---|---|
| Treatment | Δ Gloss Score | RDA | CEI |
| Ex. A/System with oscillating cup | 28.3 | 59.88 | 2.34 |
| Ex. B/System with oscillating cup | 39.6 | 72.16 | 2.45 |

TABLE 8-continued

| Summary | | | |
|---|---|---|---|
| Treatment | Δ Gloss Score | RDA | CEI |
| ISO/ADA Reference Toothbrush and Abrasive | 39.9 | 100 | 1.50 |

EMBODIMENTS

The following embodiments are contemplated. All combinations of features and embodiments are contemplated.

Embodiment 1: A meso-abrasive dentifrice formulation comprising: from 15 wt % to 30 wt % a first abrasive, and, from 10 wt % to 15 wt % a second abrasive different from the first abrasive, wherein the second abrasive is silica, and wherein wt % is based upon the total weight of the formulation.

Embodiment 2: An embodiment of embodiment 1, wherein the formulation comprises 12 wt % of the second abrasive.

Embodiment 3: An embodiment of embodiment 1 or 2, wherein the second abrasive is amorphous silica.

Embodiment 4: An embodiment of any of the embodiments of embodiment 1-3, wherein the formulation comprises from 20 wt % to 25 wt % of the first abrasive.

Embodiment 5: An embodiment of any of the embodiments of embodiment 1-4, wherein the first abrasive is pumice having an FF grade.

Embodiment 6: An embodiment of any of the embodiments of embodiment 1-5, wherein the first abrasive includes a first pumice having an FF grade and a second pumice having an ½ grade.

Embodiment 7: An embodiment of any of the embodiments of embodiment 1-6, wherein the first abrasive includes 5 wt % of the second pumice having an ½ grade.

Embodiment 8: An embodiment of any of the embodiments of embodiment 1-7, further including from 40 wt % to 50 wt % glycerin based upon the total weight of the formulation.

Embodiment 9: An embodiment of any of the embodiments of embodiment 1-8, further including from 5 wt % to 15 wt % purified water based upon the total weight of the formulation.

Embodiment 10: An embodiment of any of the embodiments of embodiment 1-9, further including at least one of sodium fluoride, calcium acetate, dibasic sodium phosphate, or combinations thereof in an amount totaling less than 10 wt %.

Embodiment 11: An embodiment of any of the embodiments of embodiment 1-10, wherein the formulation comprises:

from 15 wt % to 30 wt % a first abrasive, wherein the first abrasive is pumice selected from a first pumice of FF grade, a second pumice of ½ grade, or combinations thereof;

from 10 wt % to 15 wt % a second abrasive, wherein the second abrasive is amorphous silica;

from 40 wt % to 50 wt % glycerin;

from 5 wt % to 15 wt % purified water; and from 5 wt % to 15 wt % additional ingredients, wherein wt % is based upon the total weight of the formulation.

Embodiment 12: A system for cleaning a human oral cavity comprising: the meso-abrasive dentifrice formulation of any of embodiments 1-11, and an oscillating cup for delivery of the dentifrice formulation.

Embodiment 13: An embodiment of any of the embodiments of embodiment 1-12, wherein the oscillating cup is an oscillating rubber cup.

Embodiment 14: An embodiment of any of the embodiments of embodiment 1-13, wherein the oscillating cup oscillates reciprocally at an angle less than 360 degrees.

Embodiment 15: An embodiment of any of the embodiments of embodiment 1-14, wherein the oscillating cup oscillates reciprocally at an angle of from 45 degrees to 90 degrees.

Embodiment 16: An embodiment of any of the embodiments of embodiment 1-15, wherein the oscillating cup oscillates reciprocally at a speed of from 4000 times per minute to 11,000 times per minute.

Embodiment 17: An embodiment of any of the embodiments of embodiment 1-16, wherein the oscillating cup oscillates reciprocally at a speed of 8000 times per minute.

Embodiment 18: An embodiment of any of the embodiments of embodiment 1-17, wherein the system demonstrates at least one of:

a system Relative Dentin Abrasiveness (RDA) value less than 100;

a Pellicle Cleaning Ratio (PCR) value of greater than 125; and a Cleaning Efficiency Index (CEI) of greater than 2.00.

Embodiment 19: An embodiment of any of the embodiments of embodiment 1-18, wherein the system demonstrates a Cleaning Efficiency Index (CEI) of from 2.34 to 2.45.

Embodiment 20: An embodiment of any of the embodiments of embodiment 1-19, wherein the system demonstrates an Increase in Gloss Score of greater than 28 and a system Relative Dentin Abrasiveness (RDA) value less than 100.

While the disclosure has been described in detail, modifications within the spirit and scope of the disclosure will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the disclosure and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the disclosure.

What is claimed is:

1. A meso-abrasive dentifrice formulation comprising:

from 20 wt % to 25 wt % a first abrasive selected from a pumice of FF grade, a pumice of ½ grade, or combinations thereof, from 10 wt % to 15 wt % a second abrasive different from the first abrasive, wherein the second abrasive is a synthetic, amorphous silica having a particle size in a range of from 8 microns to 20 microns, from 45 wt % to 65 wt % total excipients, and from 5 wt % to 15 wt % ingredients for flavor, coloring, sweetness, health, and/or whitening, wherein wt % is based upon the total weight of the formulation.

2. The meso-abrasive dentifrice formulation of claim 1, wherein the formulation comprises 12 wt % of the second abrasive.

3. The meso-abrasive dentifrice formulation of claim 1, wherein the first abrasive is the pumice of FF grade.

4. The meso-abrasive dentifrice formulation of claim 1, wherein the first abrasive includes the pumice of FF grade and the pumice of ½ grade, and wherein the first abrasive includes 5 wt % of the pumice of ½ grade based upon the total weight of the formulation.

5. The meso-abrasive dentifrice formulation of claim 1, wherein the total excipients include from 40 wt % to 50 wt % glycerin and from 5 wt % to 15 wt % purified water based upon the total weight of the formulation.

6. The meso-abrasive dentifrice formulation of claim 1, wherein the ingredients for flavor, coloring, sweetness, health, and/or whitening include at least one of sodium fluoride, calcium acetate, dibasic sodium phosphate, or combinations thereof in an amount totaling less than 10 wt % based upon the total weight of the formulation.

7. The meso-abrasive dentifrice formulation of claim 1 consisting of:

from 20 wt % to 25 wt % a first abrasive selected from a pumice of FF grade, a pumice of ½ grade, or combinations thereof, from 10 wt % to 15 wt % a second abrasive different from the first abrasive, wherein the second abrasive is a synthetic, amorphous silica having a particle size in a range of from 8 microns to 20 microns, from 45 wt % to 65 wt % total excipients, and from 5 wt % to 15 wt % ingredients for flavor, coloring, sweetness, health, and/or whitening, wherein wt % is based upon the total weight of the formulation.

8. A meso-abrasive dentifrice formulation comprising:

from 20 wt % to 25 wt % a first abrasive selected from a pumice of FF grade, a pumice of ½ grade, or combinations thereof, from 10 wt % to 15 wt % a second abrasive different from the first abrasive, wherein the second abrasive is a synthetic, amorphous silica having a mass median particle size in a range of from 6.5 microns to 9.5 microns, from 45 wt % to 65 wt % total excipients, and from 5 wt % to 15 wt % ingredients for flavor, coloring, sweetness, health, and/or whitening, wherein wt % is based upon the total weight of the formulation.

9. The meso-abrasive dentifrice formulation of claim 8, wherein the formulation has a Relative Dentin Abrasiveness (RDA) value above 250 using a manual brush standard test procedure.

10. A system for cleaning a human oral cavity comprising:

the meso-abrasive dentifrice formulation of claim 1; and an oscillating cup for delivery of the dentifrice formulation.

11. The system of claim 10, wherein the oscillating cup is an oscillating rubber cup.

12. The system of claim 10, wherein the oscillating cup oscillates reciprocally at an angle less than 360 degrees.

13. The system of claim 12, wherein the oscillating cup oscillates reciprocally at an angle of from 45 degrees to 90 degrees.

14. The system of claim 10, wherein the oscillating cup oscillates reciprocally at a speed of from 4000 times per minute to 11,000 times per minute.

15. The system of claim 10, wherein the oscillating cup oscillates reciprocally at a speed of 8000 times per minute.

16. The system of claim 10, wherein the system demonstrates at least one of:

a system Relative Dentin Abrasiveness (RDA) value less than 100;

a Pellicle Cleaning Ratio (PCR) value of greater than 125; and a Cleaning Efficiency Index (CEI) of greater than 2.00.

17. The system of claim 10, wherein the system demonstrates a Cleaning Efficiency Index (CEI) of from 2.34 to 2.45.

18. The system of claim 10, wherein the system demonstrates an Increase in Gloss Score of greater than 28 and a system Relative Dentin Abrasiveness (RDA) value less than 100.

* * * * *